United States Patent [19]

Tarpley, Jr. et al.

[11] 4,198,865

[45] Apr. 22, 1980

[54] APPARATUS AND METHOD OF MONITORING ANCHORED BOLTS

[75] Inventors: William B. Tarpley, Jr., West Chester; Donald R. Culp, Norristown, both of Pa.

[73] Assignee: Energy & Minerals Research Co., Exton, Pa.

[21] Appl. No.: 927,712

[22] Filed: Jul. 24, 1978

[51] Int. Cl.² ............................................. G01N 19/01
[52] U.S. Cl. ......................................... 73/582; 73/761
[58] Field of Search ................. 73/761, 581, 582, 588, 73/594

[56] References Cited
U.S. PATENT DOCUMENTS 3,307,393  3/1967  Kessler .
3,759,090  9/1973  McFaul et al. ........................ 73/597
3,827,619  8/1974  Cusick et al. ....................... 73/582 X
4,062,227  12/1977  Heyman .
4,062,229  12/1977  Godfrey et al. .

FOREIGN PATENT DOCUMENTS 238190  11/1969  U.S.S.R. .................................. 73/581

Primary Examiner—Jerry W. Myracle
Attorney, Agent, or Firm—Seidel, Gonda, Goldhammer & Panitch

[57] ABSTRACT

The integrity of attachment of bolts in a substrate such as a wall of a mine is tested by introducing vibratory energy into an exposed end portion of the bolt and ascertaining the vibratory energy absorbed by the bolt and its attachment.

9 Claims, 10 Drawing Figures

APPARATUS AND METHOD OF MONITORING ANCHORED BOLTS

BACKGROUND

Rock bolts have been used for many years to provide support to walls and roofs in excavations, mine tunnels and other energy absorptive substrates. The bolts are often required to support very large loads. Failure to provide this support could result in injury to workers. Hence, it is important to know if the rock bolt has been properly installed. Additionally, it is desirable to determine that adequate support is being maintained at some later time after installation.

Rock bolts are generally of two types. A first type of rock bolt is the expansion shell type which uses a long bolt onto the end of which is threaded a fluted, serrated shell. This assembly is inserted into a predrilled hole in the rock and the bolt is tightened, thereby causing the shell to expand against the sides of the hole. In this manner, the tension in the bolt helps to support the rock. Present installation procedures require that the bolt be tightened to a predetermined level of torque, dependent upon such factors as rock consistency, bolt diameter, etc. Because torque is only roughly related to bolt tension (the principal variable being the thread coefficient of friction), it is an inadequate indicator of proper installation.

The second type of rock bolt is the grouted bolt. The grouted bolt includes a long cylindrical piece of metal with convolutions along its periphery similar to a rebar. The bolt is inserted into a predrilled hole in the rock along with an appropriate bonding agent such as a polyester resin. When the bonding agent has cured, the several strata of rock through which the bolt passes will effectively be joined as one with the resultant structure being stronger than any of the individual components. Where testing is employed, a torque test of 150 inch pounds is most commonly used. It has been calculated that a ⅜ inch diameter bolt bonded over only 2¼ inches of its entire length (which is normally 2-8 feet) will satisfy this requirement. Again, torque is an inadequate indicator of proper installation.

Even if proper installation has been assured, rock bolts must be periodically reinspected to ensure that adverse environmental effects such as spalling of the rock, vibration from blasting and heavy equipment, stress-corrosion cracking, etc., have not reduced the load holding capabilities of the bolts.

Heretofore, it has been suggested to evaluate the effectiveness of a rock bolt attachment by acoustic monitoring. A first group of prior art teachings are directed toward monitoring a bolt attachment by detecting a change in length of the bolt based on acoustic parameters such as impedance change (U.S. Pat. No. 3,307,393); pulse transit time (U.S. Pat. No. 3,759,090); frequency change (U.S. Pat. No. 4,062,227). The change of length of the bolt is purportedly indicative of the bolt tension. Another group of prior art teachings in the area of acoustic analysis are directed toward ascertaining a change in resonance due to the coupling of the rock to the bolt via the resin (U.S. Pat. No. 4,062,229).

SUMMARY OF THE INVENTION

In accordance with the present invention, the integrity of attachment of a bolt is tested by introducing vibratory energy into an exposed end portion of a bolt anchored in a substrate. The integrity of said attachment is ascertained as a function of the vibratory energy delivered by the bolt and its attachment to the surrounding substrate.

The present invention is predicated on the relationship that a more effective attachment between the bolt and the substrate will result in greater delivery of vibratory energy, other factors being constant. A poorly anchored bolt will deliver relatively lower levels of vibratory energy. Suitable equipment, to be described in detail hereinafter, is provided to record, exhibit, or measure the vibratory energy absorbed by the bolt and its substrate.

It is an object of the present invention to provide apparatus and method for testing the integrity of attachment of a bolt in a substrate which is based on the fact that the substrate is a relatively poor transmitter (i.e., is a good absorber) of acoustic waves as compared with the bolt whereby vibratory energy delivered by the bolt is a reliable indicator of integrity of bolt attachment to the substrate.

It is another object of the present invention to provide apparatus and method for testing the integrity of a bolt attachment to a substrate wherein the bolt may be of the expansion shell type or the grouted type.

It is another object of the present invention to provide apparatus and method for testing integrity of bolt attachment to a substrate in a manner which is reliable and requires little skill of the operator.

Other objects will appear hereinafter.

For the purpose of illustrating the invention, there is shown in the drawings a form which is presently preferred; it being understood, however, that this invention is not limited to the precise arrangements and instrumentalities shown.

Figure 1:
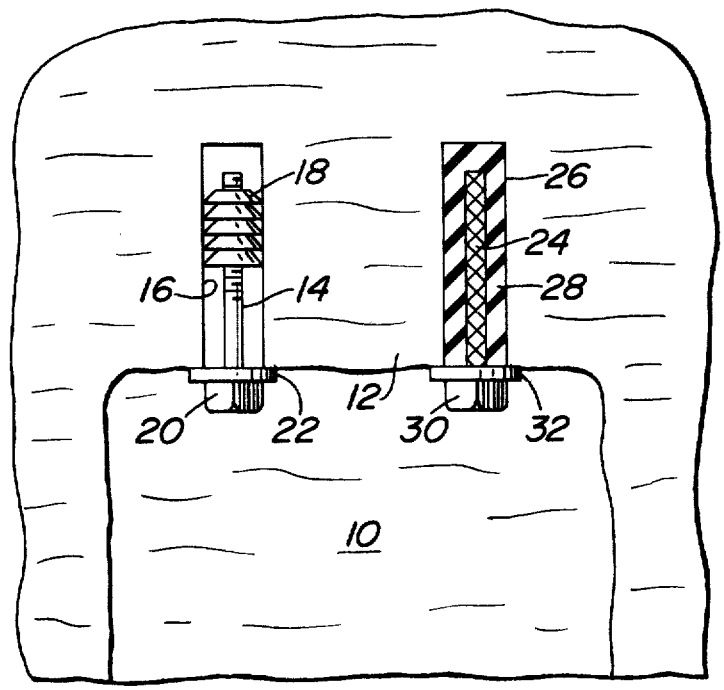
FIG. 1 is a sectional view of a mine tunnel wherein the roof has been reinforced with rock bolts of the expansion shell type and of the resin grouted type.

Referring to the drawings in detail, wherein like numerals indicate like elements, there is shown in FIG. 1 a representation of a typical environment in which the present invention may be used, namely a mine tunnel 10 having a roof 12. In the roof 12, there is represented in FIG. 1 each of the two types of rock bolts commonly found in mine tunnels. A rock bolt of the expansion type and a rock bolt of the grouted type have one thing in common, namely they are anchored into a media or substrate which when compared with the bolt alone, is a relatively poor transmitter of acoustic waves. For instance, at a frequency of 20,000 cycles per second, steel has a dissipation factor of $8.8 \times 10^{-5}$ Nepers/cm where as sandstone has been measured at $2.2 \times 10^{-3}$ Nepers/cm. This indicates that sandstone absorbs acoustic energy almost 25 times as rapidly as steel. Hence, the steel bolt may be regarded as an almost perfect transmitter of acoustic energy whereas rock may be regarded as a very efficient absorber.

In the roof 12 of the mine tunnel 10, there is illustrated in FIG. 1 a bolt 14 of the shell type mounted within the hole 16. Expansion shell 18 is attached to the threaded bolt 14 and wedged into the hole 16. The bolt 14 has a head 20 overlying a plate 22. The plate 22 has a hole through which the bolt 14 extends. The peripheral contour of plate 22 is substantially larger than that of head 20.

In the roof 12 of the mine 10, there is also illustrated a bolt 24 disposed within the hole 26. The hole 26 is filled with a resin 28 which bonds the bolt 24 in place. Bolt 24 has a head 30 which overlies and extends through a hole in the plate 32. Grout material other than resin 28 may be used.

Figure 2:
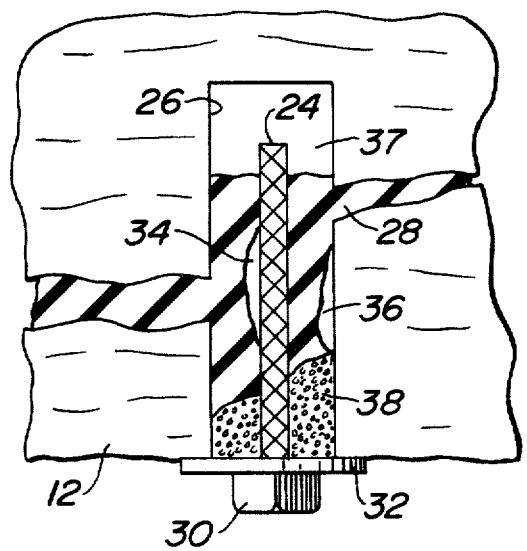
FIG. 2 is a sectional view of an improperly installed rock bolt of the resin grouted type.

The bolt 14 is of the shell type while bolt 24 is of the grouted type. Bolt 24 is typically in the form of a rebar. In FIG. 2, there is illustrated an improperly grouted resin rock bolt 24. The resin 28 has seeped into the voids of the strata which may create gaps, such as 34 immediately adjacent the periphery of bolt 24 or a gap 36 adjacent the surface of the hole 26 or gap 37 above the bolt. At 38, there is illustrated a portion of the resin 28 which is improperly cured and hence does not contribute to support of the roof rock.

The apparatus and method of the present invention may be utilized to test the integrity of the attachment of either bolt 14 or bolt 24. For purposes of illustration hereinafter, the disclosure relates to testing of the integrity of bolt 24. Bolts 14 of the shell expansion type are tested in the same manner as set forth hereinafter.

Figure 3:
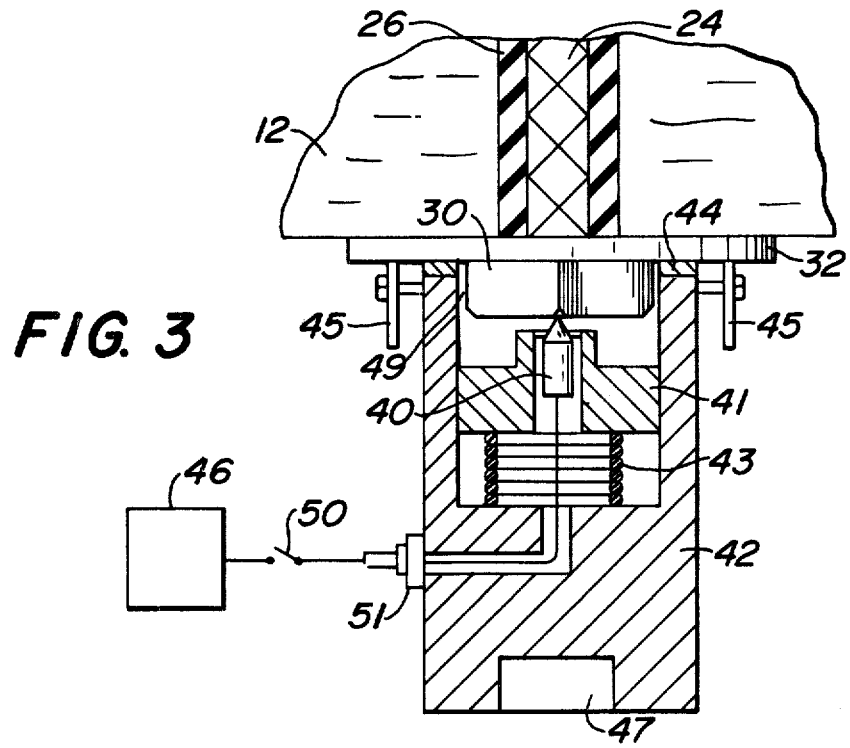
FIG. 3 is a sectional view similar to FIG. 2 but showing apparatus for vibrating the bolt to determine if it has been properly installed.

Referring to FIG. 3, vibratory energy is to be introduced into the bolt 24 by way of a transducer 40 connected to the exposed portion of head 30. Transducer 40 is an electromechanical transducer which converts high frequency electrical signals from the amplifier (a source of vibratory energy 46) into mechanical vibrations. The transducer 40 may be piezoelectric, magnetostrictive, or any other suitable type. The vibrations transmitted by transducer 40 to the bolt 24 may be longitudinal, shear, torsional, flexural, etc., depending upon the transducer design and may be in the form of a pulse, gated pulse or continuous wave depending upon the type of signals supplied by the amplifier of source 46.

The transducer 40 is coupled to the bolt head 30 in a manner so as to provide a low-loss joint. In order to maintain the transducer 40 in intimate contact with the end face of bolt 30, a clamping means is provided. The clamping means may include a support member 42 coupled to the transducer 40 but acoustically isolated therefrom such as by a force insensitive mount 41. An annular magnet 44 is connected to member 42 and is in contact with the mounting plate 32 which is made from a magnetizable material. The magnetic attraction between magnet 44 and plate 32 holds the transducer 40 in intimate contact with the bolt head 30, via the pressure applied by spring 43. This spring permits accommodation of bolts having different head heights and provides consistent contact force between the transducer 40 and the bolt head 30. The cam levers 45 are used to remove the apparatus after inspection has been completed. Cam levers 45 are pivoted to member 42.

For inspection during installation of the bolt, the support member 42 would have some means of being coupled to the installation tool, e.g., socket hole 47. Through the small clearance 49 between the support member 42 and the bolt head 30, the support member 42 may be used to rotate the bolt. Some means of delivering the electrical signal, such as a slip-ring assembly 51, is provided.

Figure 8:
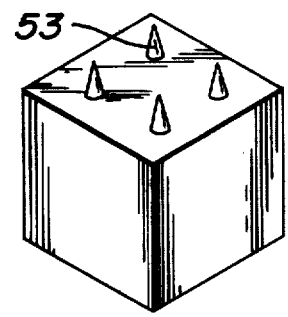
FIG. 8 is a top perspective view of an alternative transducer.

As shown in FIG. 3, the transducer 40 would be used to induce longitudinal vibrations in the bolt. FIG. 8 illustrates a simple modification of the transducer face to provide multiple contact points 53 suitable for use if torsional vibrations are desired. Four contact points are illustrated, but any number greater than two may be used for torsional vibration.

Figure 4:
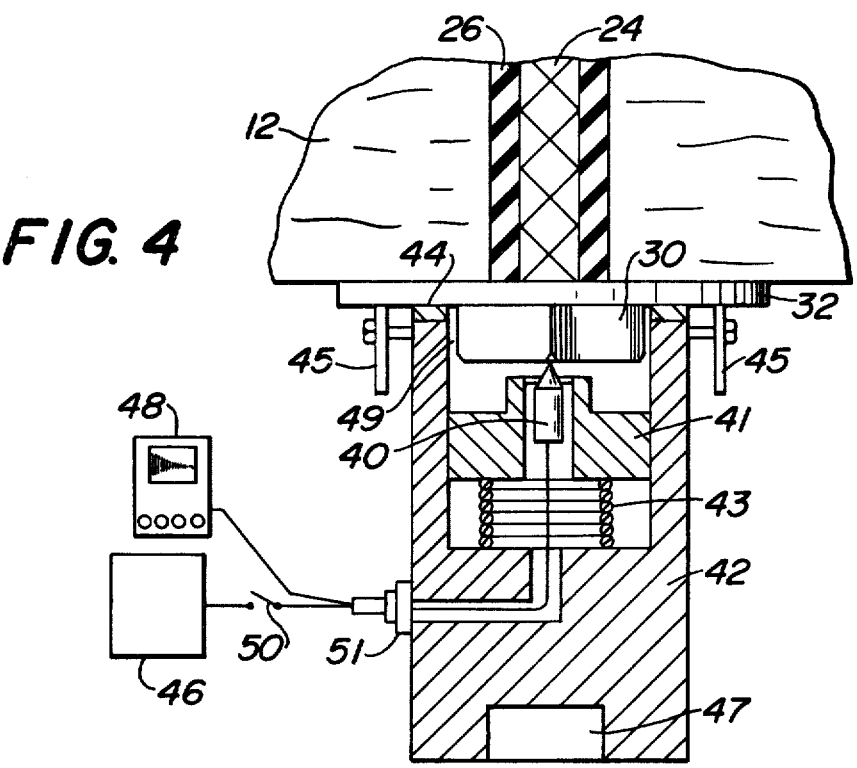
FIG. 4 is a view similar to FIG. 3 but further shows instrumentation for measuring energy delivered by the bolt.

Transducer 40 in FIG. 4 is also coupled by a conductor to an instrument, such as oscilloscope 48, to be used to determine the dissipation factor $\alpha$. There are several parameters that may be used to determine the relative energy delivered by the bolt. Among these is the system Q (defined as the ratio of energy stored to the energy dissipated per cycle (multiplied by $2\pi$), time constant $\zeta$ (defined as the time required for the vibration to decrease to 37% of its original amplitude), or dissipation factor $\alpha$ (defined as the natural log of the amplitude collapse per unit time). Since these factors are all interrelated through the energy requirements of the system, any one may be used to determine proper bolt installation. For simplicity of illustration, we shall choose $\alpha$.

The transducer 40 is coupled to the amplifier source 46 with a switch 50. If a continuous wave is used, the bolt is resonated at any of its natural frequencies. When a steady state condition has been reached, the amplifier source 46 is suddenly disconnected from the transducer 40 by opening switch 50. The oscilloscope sweep is simultaneously triggered.

Figure 5:
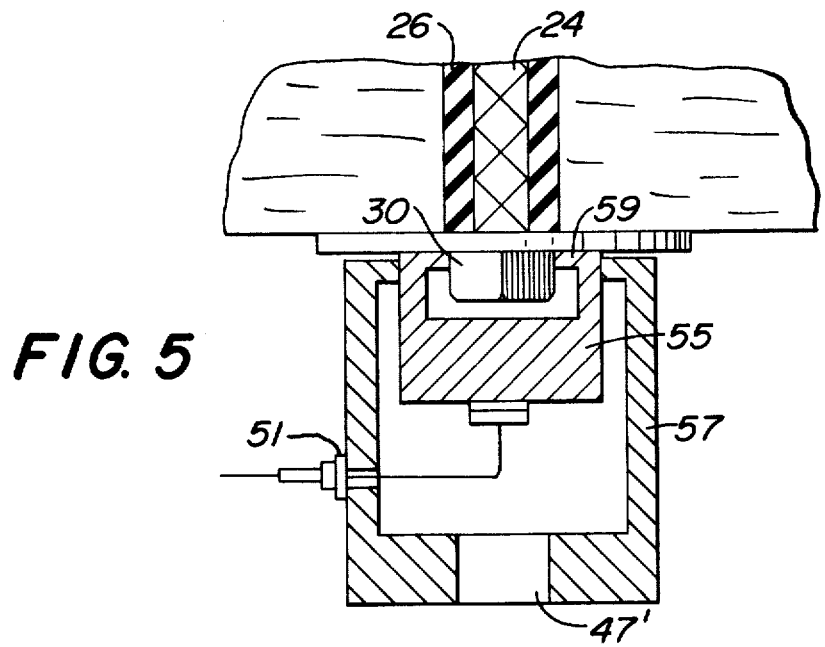
FIG. 5 is a view similar to FIG. 3 but showing an alternative construction.

If irregularities on the face of the bolt prevent coupling in the manner illustrated in FIG. 8, the method of FIG. 5 may be used. The transducer 55 is designed to just slip over the bolt head 30. The force insensitive mount 57 attaches to the transducer 55 and is provided with a means to be coupled to the installation tool, as for example socket hole 47'. When torque is applied to the transducer 55 through the force insensitive mount 57, the transducer 55 comes into intimate contact with the sides of the bolt head 30 via the protrusions 59 which may be flat, sharp or radiused as needed. Vibratory energy may then be applied to the bolt head 30 by the transducer 55.

Figure 6:
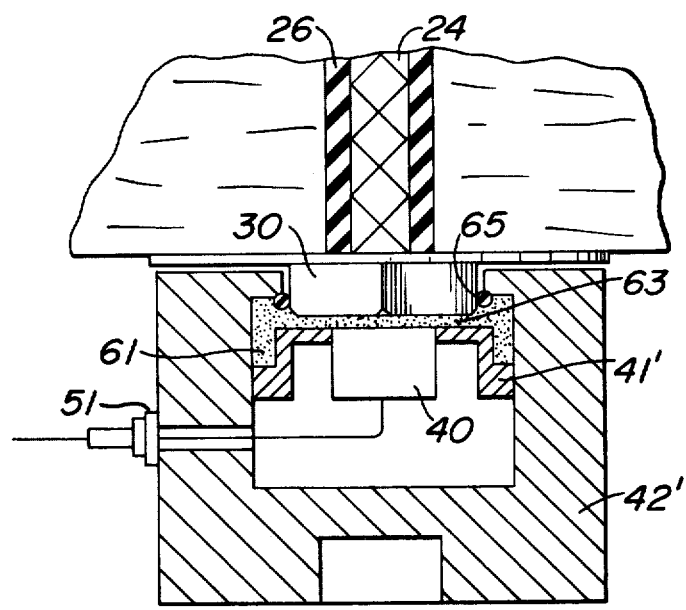
FIG. 6 is a view similar to FIG. 3 but showing an alternative construction.

FIG. 6 illustrates a method of vibrating the bolt head via a compliant coupling. The transducer 40 is isolated from the support member 42' through the force insensitive mount 41'. The compliant media 61 (which might, for example, be a grease) is contained in the cavity 63 between the transducer 40 and the bolt head 30. It is prevented from escaping by the seal 65. If necessary, the grease 61 may be pressurized to prevent cavitation. The vibration would be transmitted from the transducer 40 through the grease 61 and into the bolt head 30. Compliant media other than grease may be used.

Figure 7:
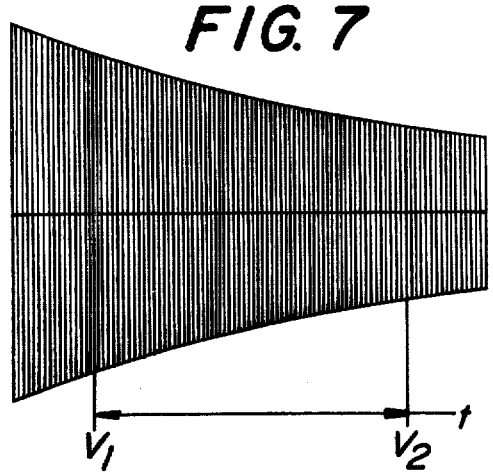
FIG. 7 is a diagrammatic view of a typical voltage trace that would be seen on an oscilloscope.

FIG. 7 shows a typical voltage trace that would be seen on the oscilloscope 48 from the output of transducer 40 as its amplitude collapses. From this trace, $\alpha$ may be calculated as follows:

$$SWR = \frac{P_+ + P_-}{P_+ - P_-}$$

$V_1$ and $V_2$ are the voltage amplitudes over a period of time t as shown in FIG. 7. As the bolt 24 becomes more solidly anchored, $\alpha$ increases. That is, the voltage decays more rapidly because energy is more rapidly absorbed by the substrate in which the bolt is mounted due to the improved coupling. Thus, $\alpha$ can be used as an indictor of quality of the rock bolt installation. Once $\alpha$ has been ascertained, the system Q is easily attained from the following formula:

$$Q = (\pi f/\alpha)$$

where f is the frequency of vibration introduced into the bolt 24 by the transducer 40. Similarly, $\zeta$ may be given as:

$$\zeta = 1/\alpha$$

It has been found for example that a 4 foot long completely unbonded resin rock bolt 24 has an $\alpha$ of 44 Nepers/second. With 10 inches of the bolt bonded by the resin 26, $\alpha$ increased to 74 Nepers/second and for 20 inches bonded increased to 100 Nepers/second. A similar response would be expected for the expansion shell rock bolt 14 as the bolt tension is increased and the shells 18 become more firmly anchored in the hole 16.

Figure 9:
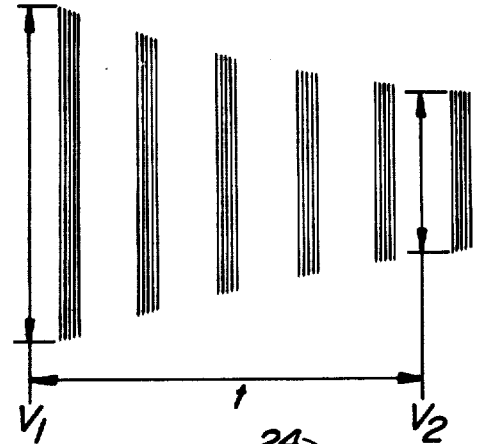
FIG. 9 is a diagrammatic view of a typical oscilloscope voltage trace of the pulse type.

In the gated-pulse mode, the amplifier source 46 would be disconnected by switch 50 and the oscilloscope 48 would be triggered just after the pulse had been triggered. FIG. 9 shows a typical oscilloscope voltage trace. Each "blip" represents voltage decay as the pulse is successively reflected from the far end of the bolt 24. From the trace shown in FIG. 9, $\alpha$ may be calculated using the same formula set forth above. It will be noted that by proper use of electronic circuits, the system Q or $\alpha$ or $\zeta$ could be given directly as a digital output eliminating the need for the oscilloscope 48 thereby improving the system portability and ease of use. In addition, a reading could be attained on an instrument with zones thereof colored red, green or yellow to indicate a bolt anchorage which is bad, good, or questionable. It will be understood by those skilled in the art that there are alternate methods, such as band width measurement, by which Q, $\alpha$ and $\zeta$ could be determined.

A second method that may be used to determine the relative acoustic energy delivered by the rock bolt to its substrate, and therefore the adequacy of installation, is the standing wave ratio indicator. As is well known, the standing wave ratio is defined by:

$$\alpha = \frac{1}{t} \ln\left(\frac{V_1}{V_2}\right)$$

where $P_+$ is the pressure transferred by the acoustic wave traveling toward the load and $P_-$ is the pressure transferred by the acoustic wave that is reflected by the load. See U.S. Pat. No. 3,288,241.

As to the significance of the standing wave ratio, consider a bolt which is poorly installed and therefore poorly coupled to the rock strata. Very little energy from the incident pressure wave $P_+$ will be transferred to the rock strata. Most of the incident pressure $P_+$ will be reflected as $P_-$ from which case $P_+$ is approximately equal to $P_-$ and the standing wave ratio will be very large. Now consider a bolt which is well installed, where considerable energy will be absorbed by the rock strata. Then $P_-$ will be much smaller than $P_+$ which is indicative of the fact that most of the incident pressure $P_+$ will be absorbed by the rock strata and very little will be reflected as $P_-$. In this case, the standing wave ratio will have decreased significantly. Thus, it is evident that bolts that are well installed will have low values of standing wave ratio.

Figure 10:
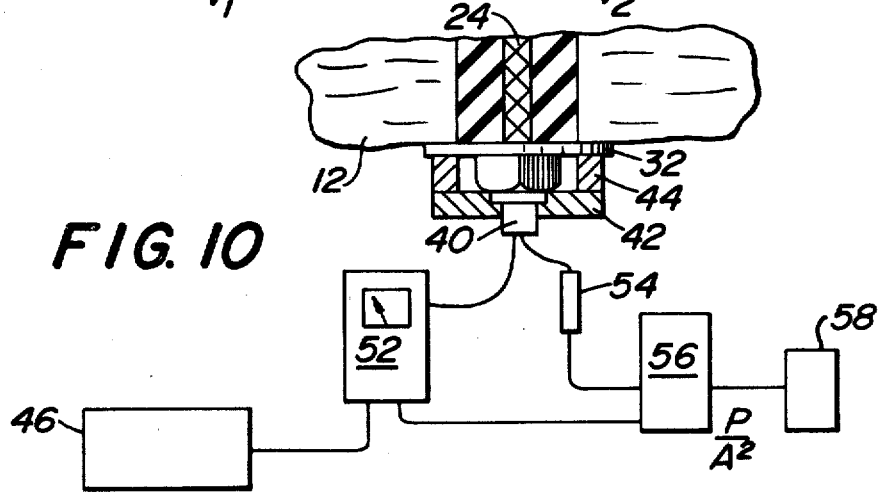
FIG. 10 is a view similar to FIG. 4 but illustrating the apparatus in accordance with another embodiment of the present invention.

Another method that may be used to determine the relative acoustic energy absorbed by the rock bolts and the surrounding substrate is direct monitoring of the power input as well as the vibrational amplitude of the transducer. The instrumentation involved is shown in FIG. 10. The source of vibratory energy 46 has an amplifier connected to the transducer 40 by way of wattmeter 52. The wattmeter 52 preferably has an output which is proportional to the net power delivered to the transducer 40 and thereby to the bolt 24. An amplitude sensor 54 is connected to the transducer 40. The amplitude sensor 54 may be any one of several types namely piezoelectric, eddy current, photoelectric, strain gauge, etc. which are suitable for high frequency pickup. The output of wattmeter 52 and sensor 54 are fed into a signal conditioner 56.

The signal conditioner 56 preferably uses a circuit for squaring the amplitude signal from sensor 54. With the amplitude signal squared, the conditioner 56 divides the same into the power signal from wattmeter 52. The ratio of input power divided by the amplitude squared is then displayed on the read-out device 58. It will be evident that for any degree of roof-rock anchoring, the input power will increase approximately as the square of the input vibrational amplitude. By taking the ratio of $P/A^2$, we have obtained a quantity which is not solely dependent upon either power or amplitude by which is determined by the coupling of the bolt 24 to the surrounding substrate by way of the resin 26. Hence, $P/A^2$ is representative of the integrity of the anchoring of the rock bolt 24.

If a bolt 14 or 24 can be vibrated, the power which is required to cause the vibration will be directly related to the integrity of the coupling between the bolt and the substrate which in turn is related to the ability of the bolt to support its load. If the integrity of the anchoring of the bolt is very low, that is, the expansion shells 18 have not expanded properly against the hole 16 or the resin 26 has not cured properly or for some other reason is inadequate, the bolt will be inadequately coupled to the substrate. Very little power will be needed to cause it to vibrate. If the integrity of the anchoring of the bolt is solid, more power will be transmitted to the surrounding substrate. Hence, an increased power requirement indicates a rock bolt which is effectively performing its intended function. As pointed out above, the power transmitted to the bolt may be ascertained by use of continuous waves, gated waves, standing wave ratio, or by monitoring the power input and vibrational amplitude.

The bolts need not be rods having a head at one end but may be any type of elongated fastener including cables. The bolt need not be embedded in a rock strata but may be a metal tension member passing through a reinforcing structure such as a concrete beam.

The intregrity of attachment of a bolt may be tested as per the present invention at the time of installation and may be tested periodically at subsequent times as part of a routine inspection.

The present invention may be embodied in other specific forms without departing from the spirit or essential attributes thereof and, accordingly, reference should be made to the appended claims, rather than to the foregoing specification, as indicating the scope of the invention.

We claim:

1. A method of testing the integrity of attachment of a bolt comprising:
   (a) introducing vibratory energy into an exposed end portion of a bolt anchored in a substrate,
   (b) ascertaining the amount of vibratory energy transmitted through the bolt and its attachment and absorbed by the substrate.

2. A method in accordance with claim 1 wherein vibratory energy is introduced into the bolt by contacting said exposed end portion of the bolt with a electromechanical transducer, and clamping the transducer into contact with said end portion of the bolt.

3. A method in accordance with claim 1 including ascertaining the amount of energy absorbed by the bolt and its substrate as a function of amplitude collapse of voltage via a suitable read-out device.

4. A method in accordance with claim 1 including ascertaining the amount of energy absorbed by the bolt and its substrate as determined by the standing wave ratio.

5. A method in accordance with claim 1 including ascertaining the amount of energy absorbed by the bolt and its substrate by dividing input power to the bolt by the square of the input amplitude.

6. Apparatus for testing the integrity of attachment of a bolt to its substrate comprising a vibratory energy transmitter for transmitting vibratory energy into an exposed portion of a bolt, clamping means associated with said transducer for clamping the transducer in a position to transmit energy to a bolt, and apparatus means coupled to said transducer for indicating the extent of energy transmitted by said bolt and absorbed by its surrounding substrate.

7. Apparatus in accordance with claim 6 wherein said clamping means includes a support for said transmitter, said transmitter being exposed at one end of said support and coupled to the support by a force-insensitive mount.

8. Apparatus in accordance with claim 7 including a magnet mounted on said support at said one end of the support.

9. Apparatus in accordance with claim 7 wherein said transmitter is spring biased toward said one end of said support.

* * * * *